United States Patent [19]

Bain et al.

[11] Patent Number: 4,916,153
[45] Date of Patent: Apr. 10, 1990

[54] MACROLID COMPOUNDS

[75] Inventors: Brian M. Bain, Tylers Green; Paul F. Lambeth, London; Alison C. Rosemeyer, Kingswood; John B. Ward, Bushey; Neil Porter, Pinner; Hazel M. Noble, Burnham; Richard A. Fletton, Ruislip; David Noble, Burnham; Derek R. Sutherland, Chalfont St Giles; Michael V. J. Ramsay, South Harrow; Edward P. Tiley, Village Way, all of England

[73] Assignee: American Cyanamid Company, Stamford, Conn.

[21] Appl. No.: 24,469

[22] Filed: Mar. 11, 1987

[30] Foreign Application Priority Data

Mar. 12, 1986 [GB] United Kingdom ............... 8606107
Mar. 12, 1986 [GB] United Kingdom ............... 8606124
Jul. 17, 1986 [GB] United Kingdom ............... 8617484
Jul. 17, 1986 [GB] United Kingdom ............... 8617483

[51] Int. Cl.$^4$ .................. A61K 31/335; C07D 313/06
[52] U.S. Cl. ......................... 514/450; 549/264
[58] Field of Search ........................ 549/264; 514/450

[56] References Cited

U.S. PATENT DOCUMENTS 3,950,360 4/1976 Aoki et al. ........................ 549/264
4,584,314 4/1986 Burckhardt ........................ 549/264

FOREIGN PATENT DOCUMENTS 0170006 2/1986 European Pat. Off. ............ 549/264

Primary Examiner—Glennon H. Hollrah
Assistant Examiner—Ba K. Trinh
Attorney, Agent, or Firm—Bacon & Thomas

[57] ABSTRACT

Compounds of formula (I):

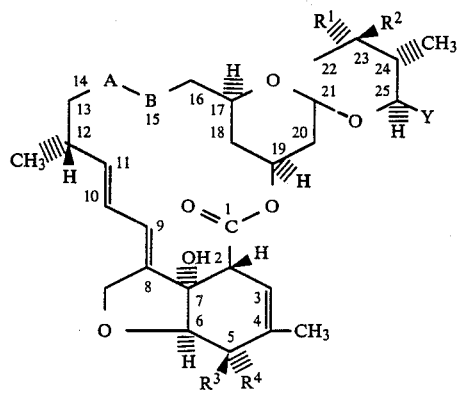

and salts thereof; wherein $R^1$ is —H, —OH or substituted —OH and $R^2$ is —H, or $R^1$ and $R^2$ together with the carbon atom to which they are attached represent C=O, C=CH$_2$ or C=NOR$^6$ in the E configuration (where $R^6$ is —H, alkyl or alkenyl);

$R^3$ is —OH or substituted —OH and $R^4$ is —H, or $R^3$ and $R^4$ together with the carbon atom to which they are attached represent C=O;

—A—B— is —C(CH$_3$)=CH— or —C(=CH$_2$)CHX— (where X is Cl or Br) and

Y is —C(R$^8$)=CHR$^7$— or —C(=CH$_2$)CHXR$^7$ (where X is Cl or Br, R$^7$ is methyl, ethyl or isopropyl and R$^8$ is C$_{2-8}$ alkyl or C$_{7-15}$ phenalkyl); with the proviso that when —A—B— is (=CH$_2$)CHX—, then Y is—C(C=CH$_2$)CHXR$^7$.

These compounds may be used for controlling insect, acarine, nematode or other pests.

12 Claims, No Drawings

MACROLID COMPOUNDS

This invention to novel antibiotic compounds and to processes for their preparation.

In our United Kingdom Patent Specification No. 2166436A we describe the production of Atibiotics S541 which may be isolated from the fermentation products of a novel Streptomyces sp. Said antibiotic compound can also be produced by fermentation of microorganism Streptomyces ssp. deposited in the Northern Regional Research Center under Accession No. NRRL 15773 as dislosed in U.S. Ser. No. 617,649, filed Jun. 5, 1984, now U.S. Pat. No. 4,869,901.

We have now found a further grouo of compounds with antibiotic activity which may be prepared by chemical modification of Antibiotics S514. The novel compounds of the invention have antibiotic activity and/or are of use as intermediates in the preparation of other active compounds.

Thus, in one aspect, the invention particularly provides the compounds of formula (I):

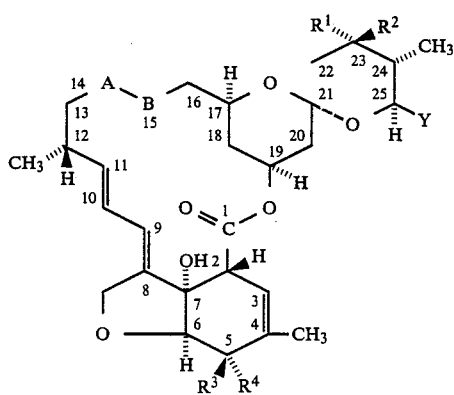

and salts thereof; wherein $R^1$ represents a hydrogen atom or a group $OR^5$ (where $OR^5$ is hydroxyl group or a substituted hydroxyl group having up to 25 carbon atoms) and $R^2$ represents a hydrogen atom or $R^1$ and $R^2$ together with the carbon atom to which they are attached represent $>C=O$, $>C=CH_2$ or $>C=NOR^6$ (where $R^6$ represents a hydrogen atom, a $C_{1-8}$ alkyl group or a $C_{3-8}$ alkenyl group and the group $>C=NOR^6$ is in the E configuration);

$R^3$ represents a group $OR^5$ as defined above and $R^4$ represents a hydrogen atom; or $R^3$ and $R^4$ together with the carbon atom to which they are attached represent $>C=O$; —A—B— represents a group

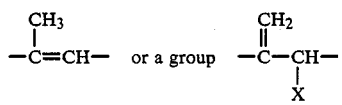

(where X represents a chlorine or bromine atom); and Y represents a group

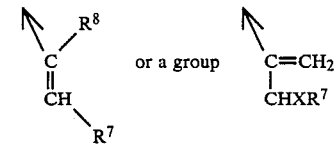

(where X is as defined above, $R^7$ represents a methyl, ethyl or isopropyl group and $R^8$ represents a $C_{2-8}$ alkyl or $C_{7-15}$ phenalkyl group); with the proviso that when —A—B— represents

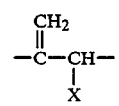

then Y represents

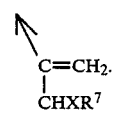

Compounds of formula (I) are of use as antibiotics. The compounds of the invention are also particularly useful as intermediates in the preparation of further active compounds. When the compounds of formula (I) are to be used as intermediates, the group —$OR^5$ will often be a protected hydroxy group and the invention particularly includes such protected compounds.

It will be appreciated that in the compounds of formula (I) the carbon atom(s) to which the atom X is attached is an asymmetric centre and formula (I) is intended to include all diastereoisomers of the compounds of the invention and all mixtures thereof including the racemates made possible by these asymmetric centres.

It will be understood that when —A—B— represents a group

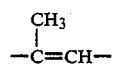

the compounds of the invention have the formula (Ia) or (1b)

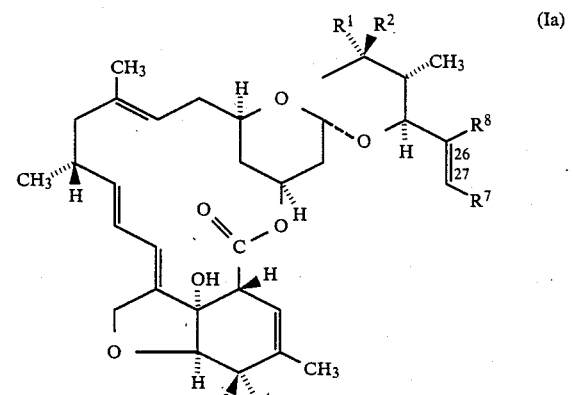

-continued

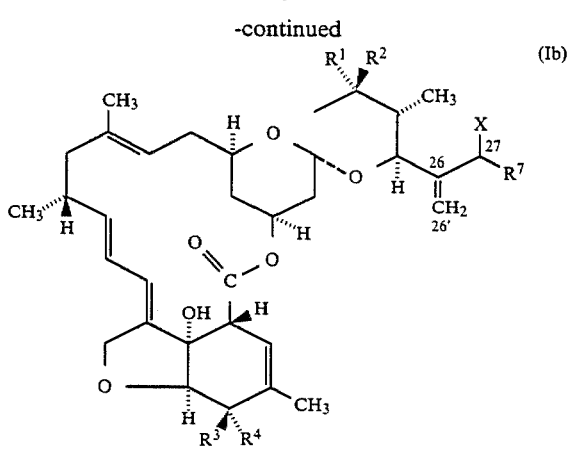

and when —A—B— represents a group

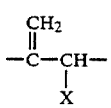

the compounds of the invention have the formula (Ic):

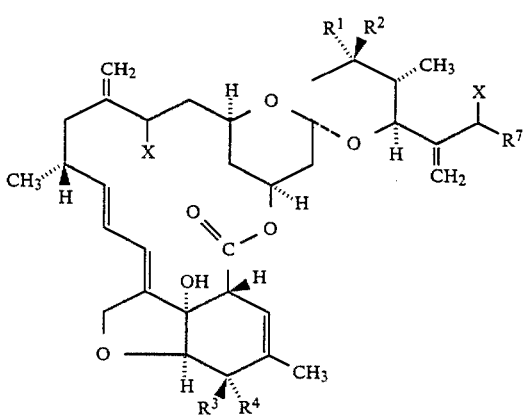

The group $R^5$ when present in compounds of formula (I) may represent an acyl group e.g. a group of the formula $R^9CO—$ or $C^9OCO—$ or $R^9OCS—$ (where $R^9$ is an aliphatic, araliphatic or aromatic group, for example an alkyl, alkenyl, alknyl, cycloalky, aralkyl or aryl group), a formyl group, a group $R^{10}$ which is as defined above for $R^9$, a group $R^{11}SO_2—$ (where $R^{11}$ is a $C_{1-4}$ alkyl or $C_{6-10}$ aryl group), a silyl group, a cyclic or acyclic acetal group, a group $—CO(CH_2)_nCO_2R^{12}$ (where $R^{12}$ is a hydrogen atom or a group as defined above for $R^9$ and n represents zero, 1 or 2) or a group $R^{13}R^{14}NCO—$ (where $R^{13}$ and $R^{14}$ may each independently represent a hydrogen atom or a $C_{1-4}$ alkyl group).

Where $R^9$ or $R^{10}$ are alkyl groups, they may be for example $C_{1-8}$ alkyl groups, e.g. methyl, ethyl, n-propyl, i-propyl, n-butyl, i-butyl, t-butyl or n-heptyl which alkyl groups may also be substituted. Where $R^9$ is a substituted alkyl group it may be substituted by, for example, one or more, eg two or three, halogen atoms (e.g. chlorine or bromine atoms), or a carboxy, $C_{1-4}$ alkoxy (e.g. methoxy, ethoxy), phenoxy or silyloxy group. Where $R^{10}$ is a substituted alkyl group it may be substituted by a cycloalkyl e.g. cyclopropyl group.

Where $R^9$ and $R^{10}$ are alkenyl or alkynyl groups, they preferably have 2-8 carbon atoms and where $R^9$ and $R^{10}$ are cycloalkyl groups, they may be for example $C_{3-12}$ cycloalkyl, such as $C_{3-7}$ cycloalkyl, e.g. cyclopentyl groups.

Where $R^9$ and $R^{10}$ are aralkyl groups, they preferably have 1-6 carbon atoms in the alkyl moiety, and the aryl group(s) may be carbocyclic or heterocyclic and preferably contain 4-15 carbon atoms e.g. phenyl. Examples of such groups include phen $C_{1-6}$ alkyl e.g. benzyl groups.

Where $R^9$ and $R^{10}$ are aryl groups, they may be carbocyclic or heterocyclic and preferably have 4-15 carbon atoms e.g. phenyl.

When $R^5$ is a group $R^{11}SO_2—$, it may be for example a methylsulphonyl or p-toluenesulphonyl group.

Where $R^5$ represents a cyclic acetal group, it may for example have 5-7 ring members as in the tetrahydropyranyl group.

When $R^5$ represents a silyl group or $R^9$ contains a silyloxy substituent, the silyl group may carry three groups which may be the same or different, selected from alkyl, alkenyl, alkoxy, cycloalkyl, aralkyl, aryl and aryloxy groups. Such groups may be as defined above and particularly include methyl, t-butyl and phenyl groups. Particular examples of such silyl groups are trimethylsilyl and t-butyldimethylsilyl.

When $R^5$ represents a group $—CO(CH_2)_nCO_2R^{12}$, it may for example be a group $—COCO_2R^{12}$ or $—COCH_2CH_2CO_2R^{12}$ where $R^{12}$ represents a hydrogen atom or a $C_{1-4}$ alkyl group (e.g. methyl or ethyl).

When $R^5$ represents a group $R^{13}R^{14}NCO—$, $R^{13}$ and $R^{14}$ for example may each independently be a hydrogen atom or a methyl or ethyl group.

When $R^6$ represents a $C_{1-8}$ alkyl group it may be for example a methyl, ethyl, n-propyl, i-propyl, n-butyl, i-butyl or t-butyl group, and is preferably a methyl group.

When $R^6$ represents a $C_{3-8}$ alkenyl group it may be for example an allyl group.

Where $R^8$ represents a $C_{2-8}$ alkyl group, it may be for example an ethyl or n-pentyl group.

Where $R^8$ represents a $C_{7-15}$ phenalkyl group, it may for example be a benzyl group.

In the compounds of formula (I) $R^7$ is preferably isopropyl.

Important compounds of formula (I) include those in which $R^1$ represents a hydroxy or ethoxy group and $R^2$ represents a hydrogen atom; or $R^1$ and $R^2$ each represents a hydrogen atom; or $R^1$ and $R^2$ together with the carbon atom to which they are attached represent $<C=O$, $<C=CH_2$ or $<C=NOCH_3$.

Further important compounds of formula (I) are those in which $R^3$ represents a hydroxy, methoxy or acetoxy group and $R^4$ is a hydrogen atom. Compound in which $R^3$ represents a hydroxy group are particularly preferred.

An important group of compounds of the invention are those of formula (Ia) in which $R^1$, $R^2$, $R^7$ and $R^8$ are as defined in Formula (I).

Important compounds of formula (Ia) include those in which $R^1$ represents a hydroxy or ethoxy group and $R^2$ represents a hydrogen atom; or $R^1$ and $R^2$ each represent a hydrogen atom; or $R^1$ and $R^2$ together with the carbon atom to which they are attached represent $<C=O$, $<C=CH_2$ or $<C=NOCH_3$.

Further important compounds of formula (Ia) are those in which $R^3$ represents hydroxy, methoxy or acetoxy and $R^4$ is a hydrogen atom. Compounds of formula (Ia) in which $R^3$ represents a hydroxy group are particularly preferred.

Important active compounds of formula (1a) are those in which: $R^1$ and $R^2$ are hydrogen atoms, $R^3$ is hydroxy, $R^4$ is hydrogen, $R^7$ is an isopropyl group and $R^8$ is an ethyl group;

$R^1$ is a hydroxy group, $R^2$ is a hydrogen atom, $R^3$ is hydroxy, $R^4$ is hydrogen, $R^7$ is an isopropyl group and $R^8$ is an ethyl group; and $R^1$ is a hydroxy group, $R^2$ is a hydrogen atom, $R^3$ is hydroxy, $R^4$ is hydrogen, $R^7$ is an isopropyl group and $R^8$ is an n-pentyl group.

As indicated previously, the compounds according to the invention may be of use as antibiotics and/or as intermediates for the preparation of further active compounds. When the compounds of the invention are to be used as intermediates, the $R^5$ group may serve as a protecting group. It will be appreciated that such a protecting group should have the minimum of additional functionally to avoid further sites of reaction and should be selectively removable. Examples of groups serving as hydroxyl protecting groups are well known and are described, for example, in "Protective Groups in Organic Synthesis" by Theodore W. Greene. (Wiley-Interscience, N.Y. 1981) and "Protective Groups in Organic Chemistry" by J. F. W. McOmie (Plenum Press, London, 1973). Examples of suitable $R^1$ and $R^3$ protecting groups include phenoxyacetyl, silyloxyacetyl, (e.g. trimethylsilyloxyacetyl and t-butyldimethylsilyloxyacetyl, and silyl such as trimethylsilyl and t-butyldimethylsilyl. Compounds of the invention containing such groups will primarily be of use as intermediates. Other groups, such as acetyl, may serve as protecting groups, but may also be present in final active compounds.

Compounds of the invention have antibiotic activity e.g. antihelminthic activity, for example against nematodes, and in particular, anti-endoparasitic and anti-ectoparasitic activity.

The compounds of the invention are therefore of use in treating animals and humans with endoparasitic and/or ectoparasitic infections.

Ectoparasites and endoparasites infect humans and a variety of animals and are particularly prevalent in farm animlas such as pigs, sheep, cattle, goats and poultry (e.g. chickens and turkeys), horses, rabbits, game-birds, caged birds, and domestic animals such as dogs, cats, guinea pigs, gerbils and hamsters. Parasitic infection of livestock, leading to anemia, malnutrition and weight loss is a major cause of economic loss throughout the world.

Example of genera of endoparasites infecting such animals and-or humans are Ancylostoma, Ascaridia, Ascaris, Aspicularis, Brugia, Bunostomum, Capillaria, Chabertia, Cooperia, Dictyocaulus, Dirofilaria, Dracunculus, Enterobius, Haemonchus, Heterakis, Loa, Nectar, Nematodirus, Nematospiroides (Heligomoroides), Nipponstrongylus, Oesophagostomum, Onchocerca, Ostertagia, Oxyuris, Parascaris, Strongylus, Strongyloides, Syphacia, Toxascaris, Toxocara, Trichonema, Trichostrongylus, Trichinella, Trichuris, Triodontophorus, Uncinaria and Wuchereria.

Examples of ectoparasites infecting animals and/or humans are arthropod ectoparasites such as biting insects, blowfly, fleas, lice, mites, sucking insects, ticks and other dipterous pests.

Examples of genera of such ectoparasites infecting animals and/or human are Ambylomma, Boophilus, Chorioptes, Culliphore, Demodex, Damalinia, Dermatobia, Gastrophilus, Haematobia, Haematopinus, Haemophysalis, Hyaloma, Hypoderma, Ixodes, Linognathus, Lucilia, Melophagus, Oestrus, Otobius, Otodectes, Psorergates, Psoroptes, Rhipicephalus, Sarcoptes, Stomoxys and Tabanus.

The compounds according to the invention have been found to be effective both in vitro and in vivo against a range of endoparasites and ectoparasites. The antibiotic activity compounds of the invention may, for example, be demonstrated by their activity against free living nematodes e.g. *Caenorhabiditis elegans*. In particular, we have found that compounds of the invention are active in vivo against parasitic nematodes such as *Nematospiroides dubius* and *Nippostrongylus braziliensis*.

Compounds of the invention are also of use as antifungals, for example, against strains of Candida sp. such as *Candida albicans* and *Candida glabrata* and against yeast such as *Saccharomyces carlsbergensis*.

Compounds of the invention are also of use in combating insect, acarine and nematodes pests in agriculture, horticulture, forestry, public health and stored products. Pests of soil and plant crops, including cereals (e.g. wheat, barley, maize and rice), cotton, tobacco, vegetables (e.g. soya), fruit (e.g. apples, vines and citrus) as well as root crops (e.g. sugarbeet, potatoes) may usefully be treated. Particular examples of such pests are fruit mites and aphids such as *Aphis fabae, Aulacorthum circumflexum, Myzus persicae, Nephotettix cincticeps, Nilparvata lugens, Panonuchus ulmi, Phorodon humuli, Phyllocoptruta oleivora, Tetranychus urticae* and members of the genera Trialeuroides; nematodes such as members of the genera Aphelencoides, Globodera, Heterodera, Meloidogyne and Panagrellus; lepidoptera such as Heliothis, Plutella and Spodoptera; grain weevils such as *Anthonomus grandis* and *Sitophilus granarius*; flour beetles such as *Tribolium castaneum*; flies such as *Musca domestica*; fire ants; leaf miners; *Pear psylla; Thrips tabaci*; cockroaches such as *Blatella germanica* and *Periplaneta americana* and mosquitoes such as *Aedes aegypti*.

According to the invention we theregfore provide compounds of formula (I) as defined above, which may be used as antibiotics. In particular, they may be used in the treatment of animals and humans with endoparasitic, ectoparasitic and/or fungal infections and in agriculture, horticulture, or forestry as pesticides to combat insect acarine and nematode pests. They may also be used generally as pesticides to combat or control pests in other circumstances, e.g. in stores, buildings or other public places or location of the pests. In general the compounds may be applied either to the host (animal or human or plants or vegetation) or a locus thereof or to the pests themselves.

Compounds of the invention may be formulated for administration in any convenient way for use in veterinary or human medicine and the invention thereof includes within its scope pharmaceutical compositions comprising a compound in accordance with the invention adapted for use in veterinary or human medicine. Such compositions may be presented for use in conventional manner with the aid of one or more suitable carriers or excipients. The compositions of the invention include those in a form especially formulated for parenteral (including intramammary administration), oral, rectal, topical or implant use. Suitable methods and agents for the formulation of compounds of the invention for use in veterinary or human medicine include those described in UK patent specification No. 2176182A.

The compounds of the invention may be administered in combination with other pharmaceutically active ingredients.

The total daily dosages of compounds of the invention employed in both veterinary and human medicine will suitably be in the range 1–2000μg/kg bodyweight, preferably from 10–1000μg/kg more preferably from 100–500μg/kg and these may be given in divided doses, e.g. 1–4 times per day.

The compounds according to the invention may be formulated in any convenient way for horticultural or agricultural use and the invention therefore includes within its scope compositions comprising a compound according to the invention adapted for horticultural or agricultural use. Such formulations include dry or liquid types, for example dusts, including dust bases or concentrates, powders, including soluble or wettable powders, granulates, including microgranules and dispersible granules, pellets, flowable, emulsions such as dilute emulsions or emulsifiable concentrates, dips such as root dips and seed dips, seed dressings, seed pellets, oil concentrates, oil solutions, injections e.g. stem injections, sprays, smokes and mites.

Suitable methods and agents for the formulation of compounds of the invention for horticultural or agricultural use include those described in UK patent specification No. 2176182A.

In the formulations, the concentration of active material is generally from 0.01 to 99% and more preferably between 0.01% and 40% by weight.

Commercial products are generally provided as concentrated compositions to be diluted to an appropriate concentration, for example from 0.001 to 0.0001% by weight, for use.

The compounds according to the invention may be prepared by a number of processes as described in the following where —A—B—, X, Y, and $R^1$ to $R^8$ are as defined for general formula (I) unless specified otherwise.

Thus, in one example, a compound of formula (Ib) or (Ic) may be prepared by treating a compound of formula (II)

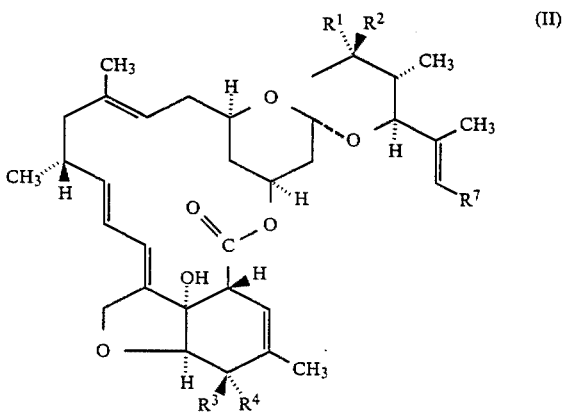

(II)

with a suitable halogenating agent.

Suitable halogenating agents include hypochlorous acid, hypobromous acid, sulphuryl chloride or N-chlorosuccinimide or N-bromosuccinimide.

Thus, a compound of formula (II) may be treated with hypochlorous or hypobromous acid in a suitable solvent such as aqueous dichloromethane at a low temperature e.g. below 10° C. Conveniently the hypochlorous or hypobromous acid may be prepared in situ from a suitable sodium or calcium hypohalite e.g. sodium hypochlorite or sodium hypobromite or calcium hypochlorite in the presence of solid carbon dioxide.

Reaction of a compound of formula (II) with sulphuryl chloride may be performed in a suitable solvent such as a halogenated hydrocarbon e.g. dichloromethane.

When N-chloro- or N-bromo- succinimide is the halogenating agent the reaction may be effected in the presence of pyridine and a catalytic amount of a diaryl diselenide such as diphenyl diselenide, dimesityl diselenide, bis(2,4,6-triisopropylphenyl)diselenide and bis(4-chlorophenyl)diselenide. Suitable solvents for the reaction include halogenated hydrocarbons e.g. dichloromethane and the reaction is conveniently carried out at a temperature in the range −20° to 50° C., preferably in the presence of a radical inhibitor e.g. 4,4′-thiobis(2-tert-butyl-6-methylphenol).

Compounds of formula (Ic) may be prepared directly from a compound of formula (II) by the halogenation process described above or via a compound of formula (Ib).

In another process, compounds of formula (I) may be prepared by interconversion of other compounds of formula (I).

Thus, for example, a compound of formula (Ia) may be prepared from a corresponding compound of formula (Ib).

In one embodiment of this process, a compound of formula (Ia) may be prepared by treating a compound of formula (Ib) with a lithium organocuprate of the formula $(R^{15})_2$CuLi (where $R^{15}$ represents a $C_{1-7}$ alkyl, phenyl or $C_{7-14}$ phenalkyl group). The reaction may be carried out in a suitable solvent such as an ether e.g. diethyl ether or tetrahydrofuran, preferably at low temperatures e.g. −78° to 0° C. Conveniently the lithium organocuprate is generated in situ from an organolithium compound $R^{15}$Li and cuprous iodide (CuI) or cuprous bromide (CuBr).

In another embodiment of this process, a compound of formula (Ia) may be prepared be treating a compound of formula (Ib) with a Grignard reagent, preferably in the presence of a vanadium salt e.g. vanadium (III) chloride. The reaction may be carried out in a suitable solvent such as a halogenated hydrocarbon eg dichloromethane, preferably at a temperature in the range −78° to 20° C.

In a further interconversion process, a compound of formula (I) in which $OR^5$ is a hydroxyl group may be prepared from a corresponding compound of formula (I) in which $R^1$ and/or $R^3$ is a group —$OR^5$ where —$OR^5$ is a substituted hydroxyl group by removal of the group $R^5$. The conversion will usually be carried out in the context of removing a protecting group such as referred to above.

Deprotection of the compounds of the invention in which —$OR^5$ represents a protected hydroxyl group can be effected by conventional methods, for example those extensively described in the aforementioned textbooks of McOmie and Greene. Thus, for example, an acyl group such as an acetyl group may be removed by basic hydrolysis, e.g. using sodium or potassium hydroxide or ammonia in an aqueous alcohol such as methanol. An acetal group such as tetrahydropyranyl may be removed for example, using acid hydrolysis (using an acid such as acetic or trifluoroacetic acid or a dilute mineral acid). Silyl groups may be removed using hydrogen fluoride in aqueous acetonitrile or an acid such as p-toluene sulphonic acid (e.g. in methanol). Arylmethyl groups may be removed by treatment with a Lewis acid (e.g. boron trifluoride-etherate) in the presence of a thiol (e.g. ethanethiol) in a suitable solvent such as dichloromethane at e.g. room temperature.

In yet another interconversion process a compound of formula (I) in which $R^1$ and $R^2$ and/or $R^3$ and $R^4$ together with the carbon atom(s) to which they are attached represent $<C=O$ may be prepared by oxidising the corresponding compound of formula (I) in which $R^1$ and/or $R^3$ is a hydroxyl group. The reaction may be effected with an oxidising agent serving to convert a secondary hydroxyl group to an oxo group, whereby a compound of formula (I) is produced. If both of $R^1$ and $R^3$ are hydroxyl groups in the starting materials for this reaction and it is desired to oxidise only one of these groups then the other is preferably protected, using protecting groups as described above, prior to the oxidation.

Suitable oxidising agents include quinones in the presence of water, e.g. 2,3-dichloro-5,6-dicyano-1,4-benzoquinone or 2,3,5,6-tetrachloro-1,4-benzoquinone; a chromium (VI) oxidising agent, e.g. pyridinium dichromate or chromium trioxide in pyridine; a manganese (IV) oxidising agent, e.g. manganese dioxide in dichloromethane; an N-halosuccinimide, e.g. N-chlorosuccinimide or N-bromosuccinimide; a dialkylsulphoxide e.g. dimethylsulphoxide, in the presence of an activating agent such as N,N'-dicyclohexylcarbodiimide or an acyl halide, e.g. oxalyl choride; or a pyridine-sulphur trioxide complex.

The reaction may conveniently be effected in a suitable solvent which may be selected from a ketone, e.g. acetone; an ether, e.g. diethyl ether, dioxan or tetrahydrofuran; a hydrocarbon, e.g. hexane; a halogenated hydrocarbon e.g. chloroform or methylene chloride; or an ester, e.g. ethyl acetate or a substituted amide e.g. dimethylformamide. Combinations of such solvents either alone or with water may also be used.

The reaction may be carried out at a temperature of from −80° C. to +50° C.

Compounds of formula (II) in which $R^1$ represents a hydrogen atom or a group $OR^5$ and $R^2$ is a hydrogen atom, or $R^1$ and $R^2$ together with the carbon atom to which they are attached represent $<C=O$, $R^3$ represents a group $OR^5$ and $R^4$ is a hydrogen atom are either known compounds described in UK patent specification No. 2176182A or may be prepared from the known compounds using methods analogous to those described therein.

Compounds of formula (II) in which $R^1$ and $R^2$ are as just defined and $R^3$ and $R^4$ together with the carbon atom to which they are attached represent $<C=O$ may be prepared from the corresponding 5-hydroxy compounds (i.e. $R^3$ is a hydroxy group and $R^4$ is a hydrogen atom) using the oxidising conditions described above.

Compounds of formula (II) in which $R^1$ and $R^2$ together with the carbon atom to which they are attached represent $<C=CH_2$ may be prepared by reacting the corresponding 23-keto compounds (i.e. compounds of formula (II) in which $R^1$ and $R^2$ together with the carbon atom to which they are attached represent $<C=O$) with an appropriate Wittig reagent e.g. a phosphorane of formula $(R^a)_3P=CH_2$ (where $R^a$ represents $C_{1-6}$ alkyl or aryl, e.g. monocyclic aryl such as phenyl). Suitable reaction solvents include ethers such as tetrahydrofuran or diethyl ether or a dipolar aprotic solvent such as dimethyl sulphoxide. The reaction may be carried out at any suitable temperature e.g. at 0° C.

Compounds of formula (II) in which $R^1$ and $R^2$ together with the carbon atom to which they are attached represent $<C=NOR^6$ [where $R^6$ is as defined in formula (I)] may be prepared from the corresponding 23-keto compounds by reaction with a reagent $H_2NOR^6$ (where $R^6$ is as just defined).

The reaction may conveniently be effected at a temperature in the range −20° to +100° C., e.g. −10° to +50° C. It is convenient to use the reagent $H_2NOR$ in the form of a salt, for example an acid addition salt such as the hydrochloride. When such a salt is employed the reaction may be carried out in the presence of an acid binding agent.

Solvents which may be employed include alcohols (e.g. methanol or ethanol), amides (e.g. N,N-dimethylformamide, N,N-dimethylacetamide or hexamethylphosporamide), ethers (e.g. cyclic ethers such as tetrahydrofuran or dioxan, and acylic such as dimethoxyethane or diethyl ether), nitriles (e.g. acetonitrile), sulphones (e.g. sulpholane) and hydrocarbons such as halogenated hydrocarbons (e.g. methylene chloride), as well as mixtures of two or more such solvents. Water may also be employed as a cosolvent.

When aqeuous conditions are employed the reaction may conveniently be buffered with an appropriate acid, base or buffer.

Suitable acids include mineral acids, such as hydrochloric or sulphuric acid, and carboxylic acid such as acetic acid. Suitable bases include alkali metal carbonates and bicarbonates such as sodium bicarbonate, hydroxides such as sodium hydroxide, and alkali metal carboxylates such as sodium acetate. A suitable buffer is sodium acetate/acetic acid.

The invention is further illustrated by the following Examples. All temperatures are in °C. The compounds are hereinafter named by reference to the known parent "Factors", Factors A and B. Factor A is a compound of formula (II) in which $R^1$ is hydroxy, $R^2$ is hydrogen, $R^3$ is hydroxy, $R^4$ is hydrogen and $R^7$ is an isopropyl group, and Factor B is a compound of formula (II) in which $R^1$ is hydroxy, $R^2$ is hydrogen, $R^3$ is methoxy, $R^4$ is hydrogen and $R^7$ is methyl. Factors A and B may be prepared as described in UK patent specification No. 2166436A.

EXAMPLE 1

27-Chloro-$\Delta^{26}$-27H-Factor B.

Factor B (1.1 g) was dissolved in redistilled dichloromethane (25 ml) and a solution of ca. 65% calcium hypochlorite (0.22 g) in distilled water (10 ml) was added. The rapidly stirred solutions were treated at room temperature with solid carbon dioxide (3 pieces, each ca. 0.3 g) and stirring was continued for 10 minutes. More calcium hypochlorite (0.1 g) and solid carbon dioxide (2 pieces, each ca 0.3 g) were added and stirring was continued at room temperature for a further 10 minutes. The organic phase was separated and the aqueous layer was extracted with dichloromethane (2×20 ml). The combined extracts were washed with water (2×20 ml), dried and evaporated to give a white foam (1.05 g) which was purified by medium pressure chromatography on silica (200 g. Merck Kieselgel 60, 230–400 mesh). Elution with n-hexane-ethyl acetate (2:1) gave the title compound (a compound of formula (Ib) in which $R^1$ is hydroxy, $R^2$ is hydrogen, $R^3$ is methoxy, $R^4$ is hydrogen, $R^7$ is isopropyl and X is chlorine) as a white foam (0.49 g); $[\alpha]_D^{22} +169°$ (c 0.55, CHCl$_3$), $\lambda_{max}$ (EtOH) 245.5 nm (E$_1$ $_{cm}$$^{1\%}$ 464); $\nu_{max}$ (CHBr$_3$) 3500 (OH) and 1710 cm$^{-1}$ (ester); δ(CDCl$_3$) includes 4.62 (d 7 Hz, 1H), 5.35 (s, 1H) and 5.53 (s, 1H); m/z includes 634,632,616,614,474,472,456,454,437,354,314,305,303,248. In a similar manner were prepared Examples 2, 3, 4, 5 and 6.

EXAMPLE 2

Chlorination of Factor A.

(a) 27-chloro-$\Delta^{26}$-27H-Factor A (a compound of formula (Ib) in which $R^1$ is hydroxy, $R^2$ is hydrogen, $R^3$ is hydroxy, $R^4$ is hydrogen, $R^7$ is isopropyl and X is chlorine) (0.43 g) as a white foam $[\alpha]_D^{22} +149°$ (c 0.43, CHCl$_3$), $\lambda_{max}$ (EtOH) 245.5 nm (E$_1$ $_{cm}$$^{1\%}$ 456); $\nu_{max}$ (CHBr$_3$) 3500 (OH) and 1710 cm$^{-1}$ (ester); δ(CDCl$_3$) includes 4.18 (d 8 Hz, 1H), 5.33 (s, 1H) and and 5.47 (s, 1H); m/z includes 648, 646, 630, 628, 593, 502, 500, 484, 482, 465, 333, 331, 301, 299, 283, 281, 255, 253.

From Factor A (1.15 g)

(b) A colourless viscous oil (0.16 g) on further chromatography on silica (100 g. Merck Kieselgel 60, 230-400 mesh), eluting with n-hexane-ethyl acetate (1:1), gave 15,27-dichloro-$\Delta^{14}$ $^{26}$-15H,27H Factor A (a compound of formula (Ic) in which $R^1$ is hydroxy, $R^2$ is hydrogen, $R^3$ is hydroxy, $R^4$ is hydrogen, $R^7$ is isopropyl and X is chlorine) as a colourless oil which slowly solidified (0.08 g); $\lambda_{max}$ (EtOH) 246.5 nm (E$_1$ $_{cm}$ $^{1\%}$ 423); $\nu_{max}$ (CHBr$_3$) 3520 (OH) and 1710 cm$^{-1}$ (ester); δ(CDCl$_3$) includes 4.17 (d 8 Hz, 1H), 4.2–4.4 (m, 2H), 5.05 (s, 1H), 5.12 (s, 1H), 5.36 (s, 1H) and 5.47 (s, 1H); m/z includes 684, 682, 680, 666, 664, 662, 648, 646, 644, 538, 536, 534, 520, 518, 516.

EXAMPLE 3

(a) 27-chloro-$\Delta^{26}$-27H Factor A 5,23-diacetate (a compound of formula (Ib) in which $R^1$ is acetoxy, $R^2$ is hydrogen, $R^3$ is acetoxy, $R^4$ is hydrogen, $R^7$ is isopropyl and X is chlorine) (1.07 g) as a white foam ($[\alpha]_D^{22} +174°$ (c 0.53, CHCl$_3$); $\lambda_{max}$ (EtOH) 245.5 nm (E$_1$ $_{cm}$$^1$ 403); $\nu_{max}$ (CHBr$_3$) 3540, 3460 (OH) and 1726 cm$^{-1}$ (ester); δ(CDCl$_3$) includes 4.22 (d 7 Hz, 1H), 5.36 (s, 1H) and 5.48 (s, 1H).

From Factor A 5,23-diacetate (3.1 g, Example 7 in UK No. 2176182A) upon chromatography eluting with toluene: ether (2:1) and further purified by chromatography eluting with dichloromethane-diethyl ether (20:1).

(b) Extended elution of the original column gave another white foam (0.67 g) which was further purified by similar chromatography on silica (400 g). Elution with dichloromethane: ether (20:1) gave 15,27-dichloro-$\Delta^{14}$ $^{26}$-15H,27H Factor A 5,23-diacetate (a compound of formula (Ic) in which $R^1$ is acetoxy, $R^2$ is hydrogen, $R^3$ is acetoxy, $R^4$ is hydrogen, $R^7$ is isopropyl and X is chlorine) as a white solid (0.14 g); $[\alpha]_D^{22} +21°$ (c 0.47, CHCl$_3$); $\lambda_{max}$ (EtOH) 247.5 nm (E$_1$ $_{cm}$$^{1\%}$ 361); $\nu_{max}$ (CHBr$_3$) 3470 (OH) and 1725 cm$^{-1}$ (ester); δ(CDCl$_3$) includes 4.1–4.25 (m, 2H) 4.34 (d 10 Hz, 1H), 5.03 (s, 1H), 5.10 (s, 1H), 5.36 (s, 1H) and 5.46 (s, 1H).

EXAMPLE 4

27-Chloro-23-deoxy-$\Delta^{26}$-27H Factor A 5-Acetate (a compound of formula (Ib) in which $R^1$ and $R^2$ are hydrogen, $R^3$ is acetoxy, $R^4$ is hydrogen, $R^7$ is isopropyl and X is chlorine) (0.13 g) as a glassy solid. $[\alpha]_D^{22} +139°$ (c 0.48, CHCl$_3$); $\lambda_{max}$ (EtOH) 245.5 nm (E$_1$ $_{cm}$$^{1\%}$ 439$\nu_{max}$(CHBr$_3$) 3540, 3475 (OH), 1734 and 1713 cm$^{-1}$ (ester); δ(CDCl$_3$) includes 4.22 (d 8 Hz, 1H), 5.27 (s, 1H) and 5.43 (s, 1H). From 23-deoxy-Factor A 5-acetate (0.2 g, Example 112 in UK No. 2176182A) upon chromatography eluting with n-hexane-ethyl acetate (4:1).

EXAMPLE 5

15,27-Dichloro-$\Delta^{14}$ $^{26}$-15H,27H Factor B (a compound of formula (Ic) in which $R^1$ is hydroxy, $R^2$ is hydrogen, $R^3$ is methoxy, $R^4$ is hydrogen, $R^7$ is isopropyl and X is chlorine) (0.07) as a white foam. $[\alpha]_D^{22} +2°$ (c 0.5, CHCl$_3$); $\lambda_{max}$ (EtOH) 245.5 nm (E$_1$ $_{cm}$$^{1\%}$ 321); $\nu_{max}$ (CHBr$_3$) 3510 (OH) and 1708 cm$^{-1}$ (ester); δ(CHCl$_3$) includes 4.33 (d 10 Hz, 1H), 4.5–4.7 (m, 3H), 5.04 (s, 1H), 5.11 (s, 1H), 5.31 (s, 1H) and 5.52 (s, 1H); m/z includes 670, 668, 666, 653, 651, 649, 510, 508, 506, 473, 471, 390, 388, 350, 348. From 27-chloro-$\Delta^{26}$-27H-factor B (0.32 g).

EXAMPLE 6

15,27-Dichloro-23-keto-$\Delta^{14}$ $^{26}$-15H,27H Factor A 5-Acetate (a compound of formula (Ic) in which $R^1$ and $R^2$ together with the carbon atom to which they are attached represent <C=O, $R^3$ is acetoxy, $R^4$ is hydrogen, $R^7$ is isopropyl and X is chlorine) (0.16 g) as a white foam. $[\alpha]_D^{22} -6°$ (c 0.59, CHCl$_3$); $\lambda_{max}$ (EtOH) 247.5 nm (E$_{1cm}$$^{1\%}$ 325); $\nu_{max}$ (CHBr$_3$) 3470 (OH) and 1720 cm$^{-1}$ (ester); δ(CDCl$_3$) includes 4.25 (d 10 Hz, 1H), 4.31 (d, 11 Hz, 1H), 5.03 (s, 1H), 5.39 (s, 1H) and 5.54 (s, 1H).

From 23-keto-Factor A 5-acetate (0.65 g, Example 18 in UK No. 2176182A) upon purification by preparative h.p.l.c. on a column packed with Spherisorb 5μ ODS-2 eluting with 85% acetone in water.

EXAMPLE 7

27-Bromo-$\Delta^{26}$-27H Factor B.

Factor B (0.11 g) was dissolved in redistilled dichloromethane (10 ml) and the solution was cooled to $-10°$ C. and sodium hypobromite (2 ml M-solution) was added. The rapidly stirred solution was treated with solid carbon dioxide (ca 0.5 g) and allowed to warm to 0° C. The reaction was worked up and purified according to the procedure of Example 1 to give the title compound (a compound of formula (Ib) in which $R^1$ is hydroxy, $R^2$ is hydrogen, $R^3$ is methoxy, $R^4$ is hydrogen, $R^7$ is isopropyl and X is bromine) as a buff solid (0.04 g); $[\alpha]_D^{22} +124°$ (c 0.3, CHCl$_3$); $\lambda_{max}$ (EtOH) 245.5 nm (E$_{1cm}$$^{1\%}$ 350); $\nu_{max}$ (CHBr$_3$) 3510 (OH) and 1710 cm$^{-1}$ (ester); δ(CDCl$_3$) includes 5.40 (s, 1H) and 5.57 (s, 1H).

EXAMPLE 8

27-Chloro-5-keto-$\Delta^{26}$-27H Factor A.

27-Chloro-$\Delta^{26}$-27H-Factor A (0.22 g) was dissolved in dichloromethane (50 ml) and stirred at room temperature with activated manganese dioxide (600 mg) for 5 days. Filtration through kieselguhr and evaporation of solvent gave a white oil (0.2 g) which was purified by medium pressure chromatography on silica (100 g Merck Kieselgel 60 230-400 mesh). Elution with n-hexane-ethyl acetate (2:1) gave the title compound (a compound of formula (Ib) in which $R^1$ is hydroxy, $R^2$ is hydrogen, $R^3$ and $R^4$ together with the carbon atom to which they are attached represent $<C=O$, $R^7$ is isopropyl and X is chlorine) as a white foam (0.17 g); $[\alpha]_D^{22} +82°$ (c 0.54, CHCl$_3$); $\lambda_{max}$ (EtOH) 227 nm ($E_{1cm}^{1\%}$ 401) and 242 nm ($E_{1cm}^{1\%}$ 333); $\nu_{max}$ (CHBr$_3$) 3510 (OH), 1714 (ester) and 1681 cm$^{-1}$ (ketone); $\delta$(CDCl$_3$) includes 4.21 (d 8 Hz, 1H), 5.36 (s, 1H) and 5.50 (s, 1H).

In a similar manner was prepared Example 17.

EXAMPLE 9

27-Chloro-$\Delta^{26}$-27H-23-deoxy Factor A.

A solution of 23-deoxy Factor A (89 mg, Example 27 in UK No. 2176182A) in dichloromethane (5 ml) was treated with a solution of calcium hypochlorite (33 mg) in water (3 ml). The mixture was stirred vigorously and small pieces of an excess of solid carbon dioxide were added portionwise. After 3 h. the mixture was diluted with water (8 ml) and dichloromethane (10 ml). The phases were separated and the aqueous layer was extracted with dichloromethane (3×) The extracts were combined with the original organic layer, washed with water (3×) then filtered through Whatman 1PS phase-separating paper, dried (magnesium sulphate) and solvent was removed under reduced pressure to give a colourless foam (91 mg). This was twice subjected to chromatography on silica (20 g, Merck Kieselgel 60, particle size 0.040–0.063 mm, 230–400 mesh) in dichloromethane-diethyl ether (4:1) to give the title compound (a compound of formula (Ib) in which $R^1$ and $R^2$ are hydrogen, $R^3$ is hydroxy, $R^4$ is hydrogen, $R^7$ is isopropyl and X is chlorine) as a colourless foam (51 mg), $[\alpha]_D^{22} +134°$ (c 0.37, chloroform), $\lambda_{max}$ (ethanol) 244 nm ($E_{1cm}^{1\%}$ 466), $\nu_{max}$ (bromoform) 3600–3350 (OH) and 1710 cm$^{-1}$ (carbonyl), $\delta$(CDCl$_3$) includes 5.28 (s, 1H), 5.44 (s, 1H), 4.23 (d 9 Hz, 1H).

EXAMPLE 10

27-Chloro-$\Delta^{26}$-27H-Factor A 23-Acetate.

A solution of 27-chloro-$\Delta^{26}$-27H-Factor A 5,23-diacetate (0.8 g) in methanol (12 ml) was cooled to 5° C. and stirred with a solution of sodium hydroxide (0.05 g) in distilled water (1.5 ml) for 1.25 hours. The reaction mixture was diluted with ether (50 ml) and washed with water (20 ml), 2N-hydrochloric acid (2×20 ml), brine (20 ml) and water (20 ml). Drying and removal of solvent gave a yellow foam (0.77 g) which was purified by medium pressure chromatography on silica (280 g. Merck Kieselgel 60, 230–400 mesh). Elution with chloroform gave the title compound (a compound of formula (Ib) in which $R^1$ is acetoxy, $R^2$ is hydrogen, $R^3$ is hydroxy, $R^4$ is hydrogen, $R^7$ is isopropyl and X is chlorine) as a white solid (0.36 g); $[\alpha]_D^{22} +169°$ (c 0.44, CHCl$_3$); $\lambda_{max}$ (EtOH) 245.5 nm ($E_{1cm}^{1\%}$ 367); $\nu_{max}$ (CHBr$_3$) 3560, 3490 (OH) and 1720 cm$^{-1}$ (ester); $\delta$(CDCl$_3$) includes 2.05 (s, 3H), 4.1–4.33 (m, 3H), 5.36 (s, 1H) and 5.49 (s, 1H).

EXAMPLE 11

27-Bromo-$\Delta^{26}$-27H-Factor A (a compound of formula (Ib) in which $R^1$ is hydroxy, $R^2$ is hydrogen, $R^3$ is hydroxy, $R^4$ is hydrogen, $R^7$ is isopropyl and X is bromine) A mixture of Factor A (612 mg), 4,4'-thio-bis(2-t-butyl-6-methyl-phenol) (7.2 mg), diphenyldiselenide (10 mg), and dry pyridine (8 μl) in dry dichloromethane (5.0 ml) was stirred under dry nitrogen, cooled in an ice-bath and treated in one portion with dry N-bromosuccinimide (232 mg). Stirring was continued at 0°–1° C. for 3 h in a dark room. More N-bromosuccinimide (232 mg) and diphenyldiselenide (10 mg) were added and stirring was continued at 0°–1° for 2.25 h. The reaction product was isolated, as described in example 12 for the chloro analogue, to give a yellow foam (837 mg). Preparative h.p.l.c. on a column packed with Spherisorb 5μODS-2, eluting with 70% acetonitrile in water afforded two major components. That eluted first was the title bromide (27-epimer 2), a light brown solid (46 mg), $[\alpha]_D^{24} +73°$ (c 0.34, chloroform); $\lambda_{max}$ (EtOH) 244 nm ($E_{1cm}^{1\%}$ 410); $\nu_{max}$ (CHBr$_3$) 3620–3350 (OH) and 1711 cm$^{-1}$ (ester); $\delta$(CDCl$_3$) includes 4.33 (d, J ca 7 Hz, 1H), 5.38 (s, 1H), and 5.54 (s, 1H). The second component was the title bromide (27-epimer 1), a pale cream solid (96.5 mg), $[\alpha]_D^{24} +145°$ (c 0.44, chloroform), $\lambda_{max}$ (EtOH) 244 nm ($E_{1cm}^{1\%}$ 419), $\nu_{max}$ (CHBr$_3$) 3505 (OH) and 1709 cm$^{-1}$ (ester); $\delta$(CbCl$_3$) includes 5.38 (s, 1H) and 5.55 (s, 1H).

EXAMPLE 12

27-Bromo-23-deoxy-$\Delta^{26}$-27H-Factor A (a compound of formula (Ib) in which $R^1$ and $R^2$ are hydrogen, $R^3$ is hydroy, $R^4$ is hydrogen, $R^7$ is isopropyl and X is bromine) Bromination of 23-deoxy Factor A (298 mg, Example 27 in UK No. 2176182A) under conditions similar to those used in Example 11, but using only one portion of N-bromosuccinimide (178 mg) for 2.5 h, followed by an almost identical product isolation gave a yellow foam (362 mg). Column chromatography on silica (145 g, Merck Kieselgel 60, 230–400 mesh) in dichloromethane-acetone (40:1) followed by preparative hplc on a column packed with Spherisorb 5μ ODS-2, eluting with 90% acetonitrile in water gave two major components. That eluted first was the title bromide (27-epimer 2), a colourless foam (24 mg), $[\alpha]_D^{22} +72°$ (c 0.18, dichloromethane); $\lambda_{max}$ (ethanol) 244 nm ($E_{1cm}^{1\%}$ 396); $\nu_{max}$ (CHBr$_3$) 3300–3620 (OH) and 1710 cm$^{-1}$ (ester); $\delta$ (CDCl$_3$) includes 4.34 (d, J ca 7 Hz, 1H), 5.34 (s, 1H) and 5.50 (s, 1H). The second component was the title bromide (27-epimer 1), a colourless foam (72 mg), $[\alpha]_D^{22} +132°$ (c 0.2, dichloromethane), $\lambda_{max}$ (ethanol) 244 nm ($E_{1cm}^{1\%}$ 460), $\nu_{max}$ (CHBr$_3$) 3300–3620 (OH) and 1710 cm$^{-1}$ (ester); $\delta$ (CDCl$_3$) includes 4.34 (d, J ca 9 Hz, 1H), 5.30 (s, 1H) and 5.49 (s, 1H).

EXAMPLE 13

26'-Methyl Factor A

To cuprous iodide (1.07 g) suspended in dry diethyl ether (2 ml) and cooled to −78° under nitrogen, was added methyl lithium (8 ml of 1.4M solution in ether). After stirring for 5 minutes, 27-chloro-$\Delta^{26}$-27H-factor A (0.18 g) in dry diethyl ether (10 ml) was added and stirring was continued at −78° under nitrogen for 3 hours, then at −2° for a further hour. The reaction mixture was allowed to warm to room temperature, poured into saturated ammonium chloride solution (200 ml) and extracted with ethyl acetate (3×75 ml). The combined extracts were washed with water (2×), brine (2×) and water, dried, and the solvent was removed to give a yellow opaque solid). This was purified by preparative h.p.l.c. on a column packed with Spherisorb 5μ ODS-2. Elution with 80% acetonitrile in water gave the title compound (a compound of formula (Ia) in which $R^1$ is hydroxy, $R^2$ is hydrogen, $R^3$ is hydroxy, $R^4$ is hydrogen, $R^7$ is isopropyl and $R^8$ is ethyl) as a white solid (0.08 g); $[\alpha]_D^{22} +126°$ (c 0.43, CHCl$_3$); $\lambda_{max}$ (EtOH) 245.5 nm ($E_{1cm}^{1\%}$ 486), $\nu_{max}$ (CHBr$_3$) 3505 (OH) and 1712 cm$^{-1}$ (ester); δ (CDCl$_3$) includes 1.09 (t 7 Hz, 3H) and 5.15 (d 10 Hz, 1H). In a similar manner was prepared Example 14:

EXAMPLE 14

26'-n-Butyl Factor A (a compound of formula (Ia) in which R$^1$ is hydroxy, R$^2$ is hydrogen, R$^3$ is hydroxy, R$^4$ is hydrogen, R$^7$ is isopropyl and R$^8$ is n-pentyl) (0.06 g) as a white powder; $[\alpha]_D^{22}$ +124° (c 0.55, CHCl$_3$); $\lambda_{max}$ (EtOH) 245.5 nm ($E_{1cm}^{1\%}$ 416); $\nu_{max}$ (CHBr$_3$) 3500 (OH) and 1712 cm$^{-1}$ (ester); δ (CDCl$_3$) includes 0.91 (t 7 Hz, 3H) and 5.16 (d 10 Hz, 1H). From 27-chloro-$\Delta^{26}$-27H-factor A (0.2 g), cuprous iodide (1.22 g) and n-butyllithium (8 ml of 1.6M solution in hexane) upon purification using preparative layer chromatography on silica plates (Merck 20 cm×20 cm precoated with Kieselgel 60 Type F-254), running twice in n-hexane-ethyl acetate (2:1).

EXAMPLE 15

26'-Phenyl Factor A.

Using a similar method to that described in Example 13, reaction of 27-chloro-$\Delta^{26}$-27H-factor A (0.2 g) with the reagent prepared from cuprous bromide (0.89 g) and phenyllithium (10 ml. of 2M solution in cyclohexane-diethyl ether) in dry tetrahydrofuran (20 ml) at 0° for 1 h and 0°-10° for 18 hours, gave, after a similar work up, a brown solid. This was purified by chromatography on silica (100 g Merck Kieselgel 60, 230–400 mesh) to give, after elution with n-hexane-ethyl acetate (1:1) a brown solid which was further purified by medium pressure chromatography on silica (80 g Merck Kieselgel 60 230–400 mesh). Elution with dichloromethane-acetone (10:1) gave the title compound (a compound of formula (Ia) in which R$^1$ is hydroxy, R$^2$ is hydrogen, R$^3$ is hydroxy, R$^4$ is hydrogen, R$^7$ is isopropyl and R$^8$ is benzyl) as white foam (0.09 g); $[\alpha]_D^{22}$ +111° (c 0.67, CHCl$_3$); $\lambda_{max}$ (EtOH) 244 nm ($E_{1cm}^{1\%}$ 409); $\nu_{max}$ (CHBr$_3$) 3620–3360 (OH) and 1713 cm$^{-1}$ (ester); δ (CDCl$_3$) includes 3.35 (d 15 Hz, 1H), 3.64 (d 15 Hz, 1H), 5.32–5.5 (m, 3H) and 7.14–7.4 (m, 5H).

EXAMPLE 16

26'-Methyl-23-deoxy Factor A

A suspension of cuprous iodide (3.029 g) in dry tetrahydrofuran (30 ml) was cooled to 0° under nitrogen and treated with a solution of methyl lithium in diethyl ether (32 ml, ca 1M). The resulting clear solution was cooled to ca −70° and treated dropwise with a solution of $\Delta^{26}$-27H-chloro-23-deoxyfactor A (500 mg) in dry tetrahydrofuran (5 ml). The mixture was stirred at −73° for 1 h then warmed to 0° and stirring was continued for a further 2 h, then poured into saturated ammonium chloride solution (500 ml). The product was extracted with ethyl acetate, washed with water, saturated sodium chloride solution and dried (MgSO$_4$). Removal of solvent gave a brown foam which was purified by preparative hplc in acetonitrile on a column of Spherisorb 5μ ODS-2. The main component was the title compound (a compound of formula (Ia) in which R$^1$ and R$^2$ are hydrogen, R$^3$ is hydroxy, R$^4$ is hydrogen, R$^7$ is isopropyl and R$^8$ is ethyl) (331 mg); $[\alpha]_D$ +132° (c 0.54, chloroform); $\lambda_{max}$ (ethanol) 244 nm ($E_{1cm}^{1\%}$ 481); $\nu_{max}$ (CHBr$_3$) 3545 and 3480 (OH) and 1708 cm$^{-1}$ (ester); δ (CDCl$_3$) includes 1.07 (t, J 7 Hz, 3H), ca 3.48 (d, J ca 9 Hz, 1H) and 5.09 (d, J 10 Hz, 1H).

EXAMPLE 17

27-Chloro-23-deoxy-5-keto-$\Delta^{26}$,27H-Factor A

From 27-chloro-$\Delta^{26}$,27H-23-desoxy Factor A. $[\alpha]_D^{22}$ +142° (c, 0.21, CH$_2$Cl$_2$). $\nu$max (CHBr$_3$) 3500 (OH), 1710 (lactone) and 1678 cm$^{-1}$ (conjugated ketone); δ (CDCl$_3$) includes 0.86 (d,5 Hz,3H), 1.00 (d,6 Hz,3H), 1.06 (d,6 Hz,3H), 1.13 (d,6 Hz,3H), 1.89 (s,3H), 3.71 (d,9 Hz,1H), 3.82 (s,1H), 3.84 (s,1H), 5.26 (m,1H), 5.42 (dd,10,14 Hz,1H), 5.29 (s,1H), 5.46 (s,1H), 6.58 (s,1H), and 4.22 (d,8 Hz,1H).

EXAMPLE 18

27-Chloro-$\Delta^{26}$, 27H-23-[E]-Methoxyimino Factor A

A solution of 23-[E]-methoxyimino Factor A (640 mg) in redistilled dichloromethane (15 ml) was stirred vigorously. A suspension of calcium hypochlorite (133 mg) in water (5 ml) was added. Small pieces of solid carbon dioxide were added over 45 min. The mixture was stirred vigorously for a further 18 h. The organic layer was collected. 2M Hydrochloric acid (2 ml) was added to the aqueous layer which was then extracted with dichloromethane (2×50 ml). The extracts were combined, washed successively with 50 ml portions of water and brine and dried (MgSO$_4$). Removal of solvent gave a white foam which was purified by medium pressure column chromatography on silica gel (300 g Merck Kieselgel 60, 230–400 mesh). Elution with 10:1 dichloromethane:diethyl ether gave a product (123 mg). This was further purified by preparative hplc on a column packed with Sperisorb 5μ ODS-2. Elution with 90% acetonitrile in water gave the title compound as a white foam (70 mg). $[\alpha]_D^{22}$ +152° (c,0.19, CH$_2$Cl$_2$); $\lambda$max (EtOH) 244.4 nm (ε26940); $\nu$max (CHBr$_3$) 3540, 3460 (OH) and 1708 cm$^{-1}$ (lactone); δ (CDCl$_3$) includes 1.00 (d,6 Hz,3H), 1.06 (d,6 Hz,6H), 1.16 (d,6 Hz,3H), 1.87 (s,3H), 1.96 (d,14 Hz,1H), 3.33 (d,14 Hz,1H), 3.87 (s,3H), 3.90 (d,11 Hz,1H), 4.26 (m,2H), 5.35 (s,1H) and 5.52 (s,1H).

EXAMPLE 19

26'-Ethyl Factor A

A solution of ethylmagnesium bromide (1.0 ml of a 3M solution in diethyl ether) was added dropwise over 10 min to a slurry of vanadium (III) chloride (486 mg) in dichloromethane (6 ml) stirring at −78° under nitrogen. After 20 min a solution of $\Delta^{26}$-27H-27-chloro Factor A (200 mg) in dichloromethane (2 ml) was added, and the reaction mixture left stirring at −78° for 90 min, then for a further 20 h at room temperature. The reaction mixture was poured into saturated sodium bicarbonate solution (50 ml), dichloromethane (50 ml) added, and the resulting mixture filtered through kieselguhr. The organic phase was collected and further extraction with dichloromethane (3×50 ml) carried out. The organic phase was dried (MgSO$_4$) and solvent removed to give a foam (185 mg) which was purified by preparative hplc to give the title compound as a cream foam (10 mg). δ (CDCl$_3$) includes 0.82 (d,6 Hz,3H), 0.91–1.1 (m,12H), 1.88 (s,3H), 3.78 (d,10 Hz,1H), 3.96 (d,5 Hz,1H), 4.29 (t,5 Hz,1H), 5.18 (d,9 Hz,1H).

The following are examples of formulations according to the invention. The term "Active Ingredient" as used hereinafter means a compound of the invention.

| Multidose parenteral injection | | |
| --- | --- | --- |
| | % w/v | Range |
| Active Ingredient | 4.0 | 0.1–7.5% w/v |
| Benzyl alcohol | 2.0 | |
| Glyceryl triacetate | 30.0 | |
| Propylene glycol | to 100.0 | |

Dissolve the active ingredient in the benzyl alcohol and glyceryl triacetate. Add propylene glycol and make up to volume. Sterilise the product by conventional pharmaceutical methods, for example sterile filtration or by heating in an autoclave and package aseptically.

| Aerosol spray | | |
| --- | --- | --- |
| | % w/w | Range |
| Active Ingredient | 0.1 | 0.01–2.0% w/w |
| Trichloroethane | 29.9 | |
| Trichlorofluoromethane | 35.0 | |
| Dichlorodifluoromethane | 35.0 | |

Mix the Active Ingredient with trichloroethane and fill into the aerosol container. Purge the headspace with the gaseous propellant and crimp the valve into position. Fill the required weight of liquid propellant under pressure through the valve. Fit with actuators and dust-caps.

| Tablet Method of manufacture - wet granulation | |
| --- | --- |
| | mg |
| Active Ingredient | 250.0 |
| Magnesium stearate | 4.5 |
| Maize starch | 22.5 |
| Sodium starch glycolate | 9.0 |
| Sodium lauryl sulphate | 4.5 |
| Microcrystalline cellulose | to tablet core weight of 450 mg |

Add sufficient quantity of a 10% starch paste to the active ingredient to produce a suitable wet mass for granulation. Prepare the granules and dry using a tray or fluid-bed drier. Sift through a seive, add the remaining ingredients and compress into tablets.

If required, film coat the tablet cores using hydroxypropylmethyl cellulose or other similar film-forming material using either an aqueous or non-aqueous solvent system. A plasticizer and suitable colour may be included in the film-coating solution.

| Veterinary tablet for small/domestic animal use Method of manufacture - dry granulation | |
| --- | --- |
| | mg |
| Active Ingredient | 50.0 |
| Magnesium stearate | 7.5 |
| Microcrystalline cellulose to tablet core weight of | 75.0 |

Blend the active ingredient with the magnesium stearate and microcrystallise cellulose. Compact the blend into slugs. Break down the slugs by passing through a rotary granulator to produce free-flowing granules. Compress into tablets.

The tablet cores can then be film-coated, if desired, as described above.

| Veterinary intrammary injection | | | |
| --- | --- | --- | --- |
| | | mg/dose | Range |
| Active Ingredient | | 150 mg | 0.05–1.0 g |
| Polysorbate 60 | 3.0% w/w | to 3 g | to 3 or 15 g |
| White Beeswax | 6.0% w/w | | |
| Arachis oil | 91.0% w/w | | |

Heat the arachis oil, white beeswax and polysorbate 60° to 160° C. with stirring. Maintain at 160° C. for two hours and then cool to room temperature with stirring. Aseptically add the active ingredient to the vehicle and disperse using a high speed mixer. Refine by passing through a colloid mill. Aseptically fill the product into sterile plastic syringes.

| Veterinary oral drench | | |
| --- | --- | --- |
| | % w/v | Range |
| Active Ingredient | 0.35 | 0.01–2% w/v |
| Polysorbate 85 | 5.0 | |
| Benzyl alcohol | 3.0 | |
| Propylene glycol | 30.0 | |
| Phosphate buffer | as pH 6.0–6.5 | |
| Water | to 100.0 | |

Dissolve the active ingredient in the Polysorbate 85, benzyl alcohol and the propylene glycol. Add a proportion of the water and adjust the pH to 6.0–6.5 with phosphate buffer, if necessary. Make up to final volume with the water. Fill the product into the drench container.

| Veterinary oral paste | | |
| --- | --- | --- |
| | % w/w | Range |
| Active Ingredient | 7.5 | 1–30% w/w |
| Saccharin | 25.0 | |
| Polysorbate 85 | 3.0 | |
| Aluminum distearate | 5.0 | |
| Fractionated coconut oil | to 100.0 | |

Disperse the aluminium distearate in the fractionated coconut oil and polysorbate 85 by heating. Cool to room temperature and disperse the saccharin in the oily vehicle. Dispense the active ingredient in the base. Fill into plastic syringes.

| Granules for veterinary in-feed administration | | |
| --- | --- | --- |
| | % w/w | Range |
| Active Ingredient | 2.5 | 0.05–5% w/w |
| Calcium sulphate, hemi-hydrate | to 100.0 | |

Blend the Active Ingredient with the calcium sulphate. Prepare the granules using a wet granulation process. Dry using a tray or fluid-bed drier. Fill into the appropriate container.

| Emulsifiable Concentrate | |
| --- | --- |
| Active ingredient | 50 g |
| Anionic emulsifier (e.g. Phenyl sulphonate CALX) | 40 g |
| Non-ionic emulsifier (e.g. Syperonic NP13) | 60 g |
| Aromatic solvent (e.g. Solvesso 100) | to 1 liter. |

Mix all ingredients, stir until dissolved.

| Granules | | |
|---|---|---|
| (a) | Active ingredient | 50 g |
| | Wood resin | 40 g |
| | Gypsum granules (20–60 mesh) (e.g. Agsorb 100A) | to 1 kg |
| (b) | Active ingredient | 50 g |
| | Syperonic NP13 | 40 g |
| | Gypsum granules (20–60 mesh) | to 1 kg. |

Dissolve all ingredients in a volatile solvent e.g. methylene chloride, add to granules tumbling in mixer. Dry to remove solvent.

We claim:

1. Compounds of formula (I):

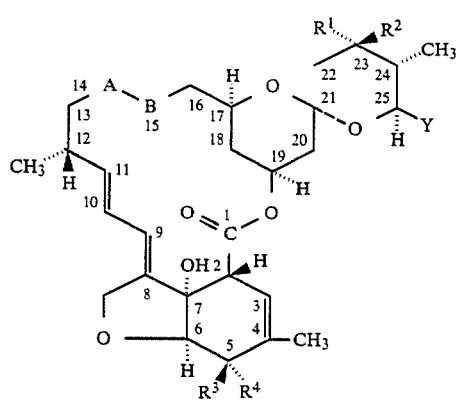

and salts thereof; wherein $R^1$ is a group $OR^5$, where the group $R^5$ may represent an acyl group of the formula $R^9CO—$ or $R^9OCO—$ or $R^9OCS—$, where $R^9$ is an alkyl, alkenyl, alkynyl, cycloalkyl, aralkyl or aryl group; a formyl group, a group $R^{10}$ which is as defined above for $R^9$, a group $R^{11}SO_2—$, where $R^{11}$ is a $C_{1-4}$ alkyl or $C_{6-10}$ aryl group, a silyl group, a cyclic or acyclic acetal group, a group $—CO(CH_2)_nCO_2R^{12}$, where $R^{12}$ is a hydrogen atom or a group as defined above for $R^9$ and n represents zero, 1 or 2; or a group $R^{13}R^{14}NCO—$ where $R^{13}$ and $R^{14}$ may each independently represent a hydrogen atom or a $C_{1-4}$ alkyl group, and $R^2$ is a hydrogen atom or $R^1$ and $R^2$ together with the carbon atom to which they are attached represent $<C=CH_2$ or $<C=NOR_6$ where $R_6$ is a hydrogen atom, $C_{1-8}$ alkyl group or a $C_{3-8}$ alkenyl group and the group $CNOR_6$ is in the E configuration;

$R^3$ is a group $OR^5$ as defined above and $R^4$ is a hydrogen atom; or $R^3$ and $R^4$ together with the carbon atom to which they are attached represent $<C=O$; $—A—B—$ is (i) a group

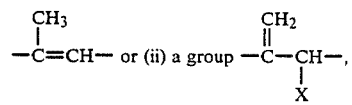 or (ii) a group 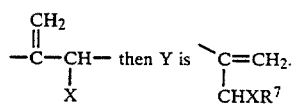, where X is a chlorine or bromine atom; and Y is a group

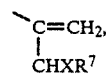

where X is as defined above, $R^7$ is a methyl, ethyl or isopropyl group; with the proviso that when $—A—B—$ is $$-\overset{\overset{CH_2}{\|}}{\underset{X}{C}}-CH- \text{ then Y is } \overset{C=CH_2}{\underset{CHXR^7}{}}.$$

2. Compounds according to claim 1 in which $R^7$ is an isopropyl group.

3. Compounds according to claim 1 in which $R^1$ is ethoxy group and $R^2$ is a hydrogen atom; or $R^1$ and $R^2$ together with the carbon atom to which they are attached represent $<C=CH_2$ or $<C=NOCH_3$.

4. Compounds according to claim 1 in which $R^3$ is a hydroxyl, methoxy or acetoxy group and $R^4$ is a hydrogen atom.

5. Compounds according to claim 1 in which $R^3$ is a hydroxyl group and $R^4$ is a hydrogen atom.

6. Compounds according to claim 1 in which $—A—B—$ is a group (i).

7. Compounds according to claim 6 in which $R^1$ is a ethoxy group and $R^2$ is a hydrogen atom; or $R^1$ and $R^2$ together with the carbon atom to which they are attached represent $<C=CH_2$ or $<C=NOCH_3$; and $R^3$ is hydroxy, methoxy or acetoxy group and $R^4$ is a hydrogen atom.

8. A composition for use in human medicine containing an effective amount of at least one compound according to claim 1 together with one or more carries and/or excipients.

9. A composition for use in veterinary medicine containing an effective amount of at least one compound according to claim 1 together with one or more carriers and/or excipients.

10. A pest control composition containing an effective amount of at least one compound according to claim 1 together with one or more carriers and/or excipients.

11. A method for combatting pests in agriculture, horticulture of forestry, or in stores, buildings or other public places or locations of the pests, which comprises applying to plants or other vegetation or to the pests themselves or a location thereof an effective amount of one or more compounds according to claim 1.

12. A method as claimed in claim 11 in which said pests are insect, acarine or nematode pests.

* * * * *